United States Patent
Goldstein et al.

(10) Patent No.: US 8,001,966 B1
(45) Date of Patent: Aug. 23, 2011

(54) CONTINUOUS POSITIVE AIRWAY SUPPLY SYSTEM TO NASAL CANNULA

(75) Inventors: Mitchell Goldstein, Northridge, CA (US); Arnold M. Heyman, Los Angeles, CA (US)

(73) Assignee: Neotech Products, Inc., Valencia, CA (US)

( * ) Notice: Subject to any disclaimer, the term of this patent is extended or adjusted under 35 U.S.C. 154(b) by 1090 days.

(21) Appl. No.: 11/784,671

(22) Filed: Apr. 10, 2007

Related U.S. Application Data

(60) Provisional application No. 60/850,410, filed on Oct. 10, 2006.

(51) Int. Cl.
*A61M 11/00* (2006.01)

(52) U.S. Cl. .......... 128/204.18; 128/204.21; 128/204.22

(58) Field of Classification Search ............. 128/204.18, 128/204.21, 204.22, 204.26, 204.29
See application file for complete search history.

*Primary Examiner* — Steven O Douglas
(74) *Attorney, Agent, or Firm* — William W. Haefliger

(57) ABSTRACT

The invention concerns a combination control for use in nasal cannula therapy, and includes a high flow, nasal cannula respiratory assistance ducted system.

10 Claims, 5 Drawing Sheets

CONTINUOUS POSITIVE AIRWAY SUPPLY SYSTEM TO NASAL CANNULA

This regular application is based on provisional application No. 60/850,410, filed Oct. 10, 2006.

BACKGROUND OF THE INVENTION

This invention relates generally to nasal cannula therapy, and more particularly to improvements concerning fluid flow in nasal cannula therapy systems.

Nasal continuous positive airway pressure, NCPAP, is a used standard for administration of non-invasive positive airway pressure in the Neonate. Historically, Nasal Cannulae have been used at low flow rates (<1.5 l pm) during infant weaning from assisted ventilation, or for maintenance in the sub-acute phase of chronic lung disease. Difficulty in regulation of pressure, and concerns regarding the damaging effects of inadequately warmed and humidified oxygen delivery systems on nasal mucosa, precluded the use of these devices in the more acute phases of respiratory distress and at the higher liter flow rates that would have been required to generate the pressures necessary to provide for that particular disease process. Certain devices held the promise of improved humidification and warming of the cannula flow, but introduced the possible deleterious effect of unknown pressure propagation as well as reported bacteria contamination of the circuit.

Accordingly, there was concern about delivering pressures that were excessive and possibly damaging to the respiratory tract, sinuses, ear drum or GI tract. Mechanical ventilators used for monitoring for pressures and flow were excessively expensive to supply and operate.

SUMMARY OF THE INVENTION

It is a major object of the invention to provide solutions to the described problems and difficulties. Basically, the invention is embodied in a combination control including monitoring for use in nasal cannula therapy, that comprises:

a) a high flow, nasal cannula respiratory assistance ducted system, b) the system including the following ii) means and at least one or both of the following i) means and iii) means, i) flow metering first means associated with said system ducting, upstream of the nasal cannula, ii) safety pressure release valve second means also associated with said system ducting, downstream of the nasal cannula, iii) flow metering third means associated with the system ducting, and downstream of the nasal cannula.

Another object of the invention includes provision, and in series sequence, of:

i) an oxygen gas source, ii) means receiving oxygen from said source, and air, for blending air, oxygen, and/or nitric oxide, in an output stream, iii) a heater/humidifier to heat and humidify said stream, iv) a nasal cannula to receive the heated and humidified stream, for administration to the infant or patient.

A further object includes provision of a bypass outlet from the system for flow to the patient, downstream of said first means.

Yet another object includes provision of a proportioning valve extending at a system outlet, and operating as said second means.

Another object of the present invention is to provide for requisite warmth and humidification of the air stream. The complications of inadvertent pressure propagation are avoided. NCPAP is not needed for pressure regulation. Flow regulation occurs without attendant pressure effects. The device allows for demand flow without using a conventional ventilator and subsequent costs.

These and other objects and advantages of the invention, as well as the details of an illustrative embodiment, will be more fully understood from the following specification and drawings, in which:

DRAWING DESCRIPTION

DETAILED DESCRIPTION

Figure 1:
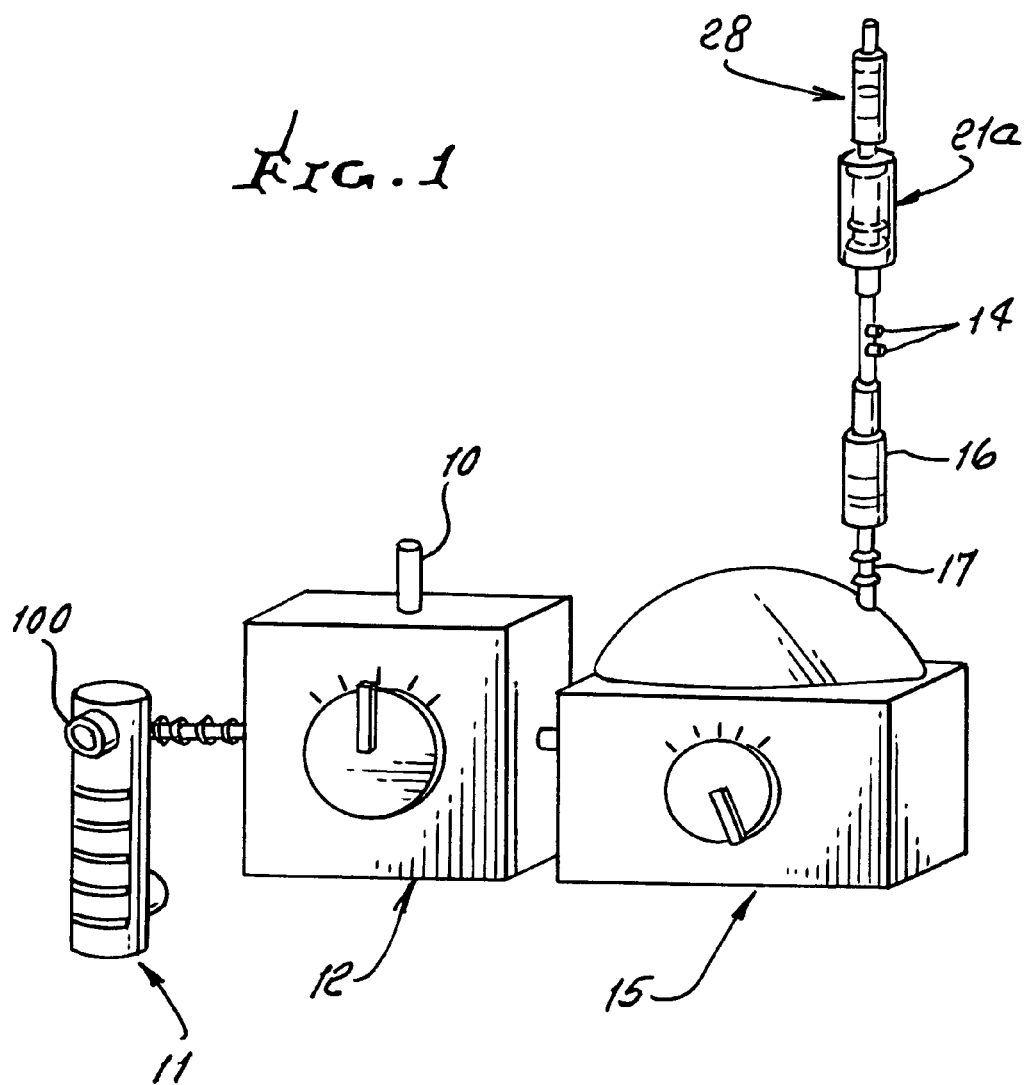
FIG. 1 is a system diagram.

Referring first to FIG. 1, showing a preferred system, air supplied at 10, and oxygen supplied at 100 enter a blending zone 12, to be thoroughly mixed or blended. A control 11 to increase or decrease flows from the oxygen supply 100 is shown. The flowing mix passes to a flow meter at 16 via a warmer/humidifier 15, which may consist of warm water into which the flow is injected to bubble up and continue flowing as at 17, as warmed, humidified air/oxygen blend. Some of the flow passes to the small tubes or prongs 14 for supply to the infant's lungs. Some of that supply may variably leak to atmosphere, via the nostrils or expelled via the infant's mouth, for example along with flow expelled from the lungs, during breathing. Flow pressure supplied to the cannula is desirably below about 10 cm water pressure. The oxygen supply, as at hospital wall outlet 100, is typically about 50 psi (3,154 cm/$H_2O$).

Figure 4:
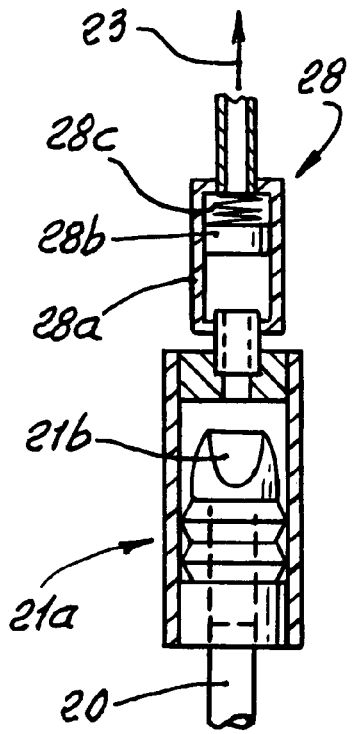
FIG. 4 is a section taken through a pressure relief flutter type valve, in a system.

Remnant air passes in duct 20 FIG. 4 to an outlet, such as a "pop-off" valve. The latter preferably takes the form of a proportioning valve, seen at 21$a$ in FIG. 4, and having elastomeric flow control sections 21$b$ that excessive air pressure forcibly spread apart, for example to suddenly discharge the flow when the pressure exceeds about 10 cm water pressure. See also arrow 23, indicating discharge to atmosphere. Need for means to maintain pressure in the duct at or near 10 cm of water derives from the infant's lungs, which should not be subjected to excessive pressure. Such excessive pressure could arise as from closing of the infant's mouth or covering of its nostrils, or both, excessive pressure being variably transmitted to 21$a$. Proportioning valve 21 or 21$a$ is herein designated at times as a form of pressure relief "second means".

Figure 5:
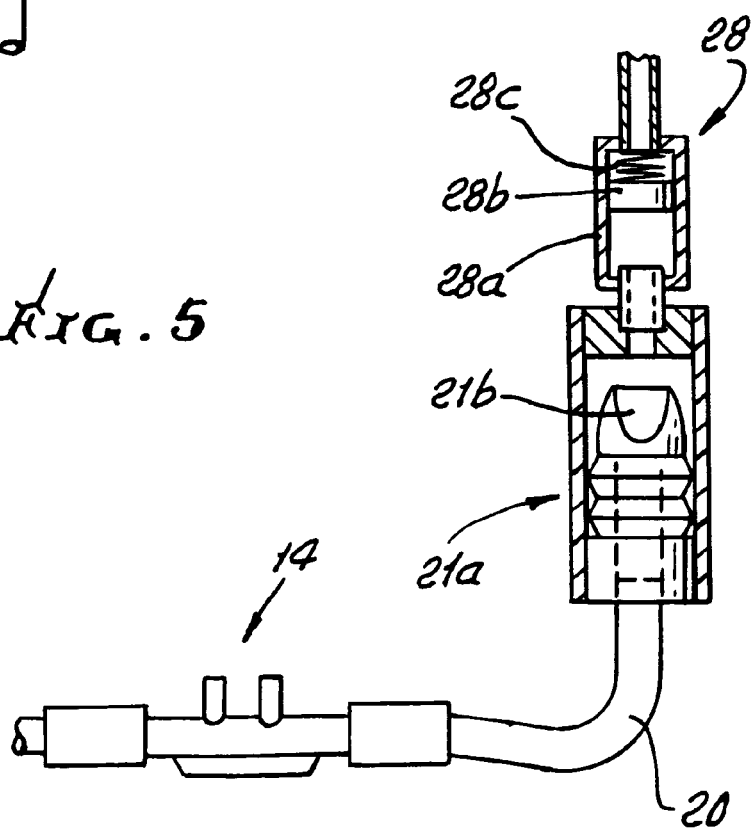
FIG. 5 is a view showing system ducting, a pressure relief valve in series in the ducting; and a flow meter downstream of the pressure relief valve.
Figure 6:
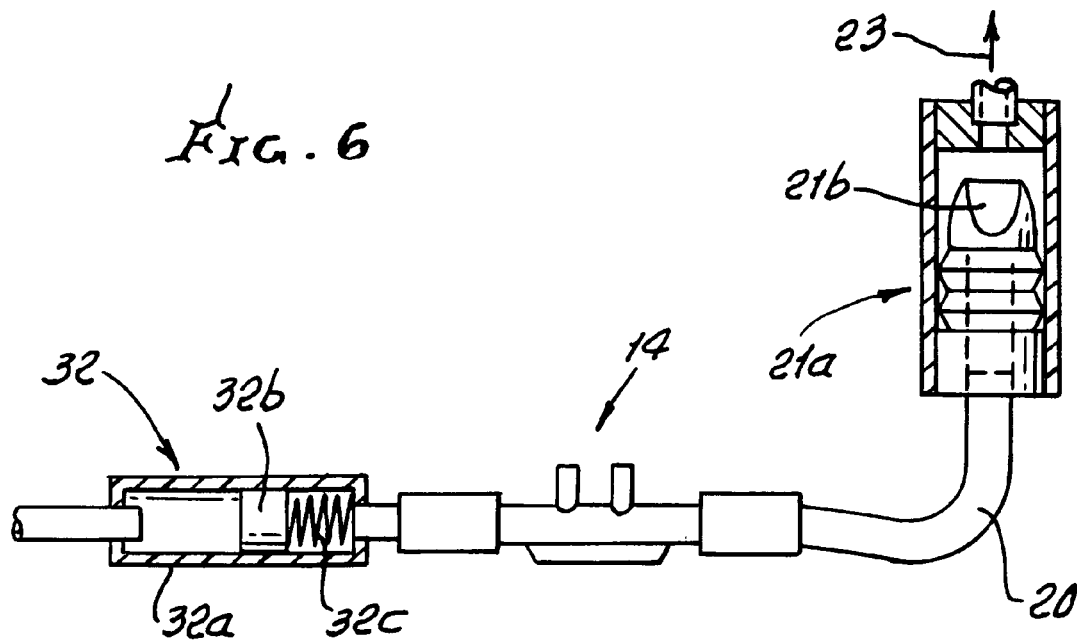
FIG. 6 is a view showing system ducting, a pressure relief valve in series in the ducting, and a flow meter upstream of cannula in the ducting.
Figure 7:
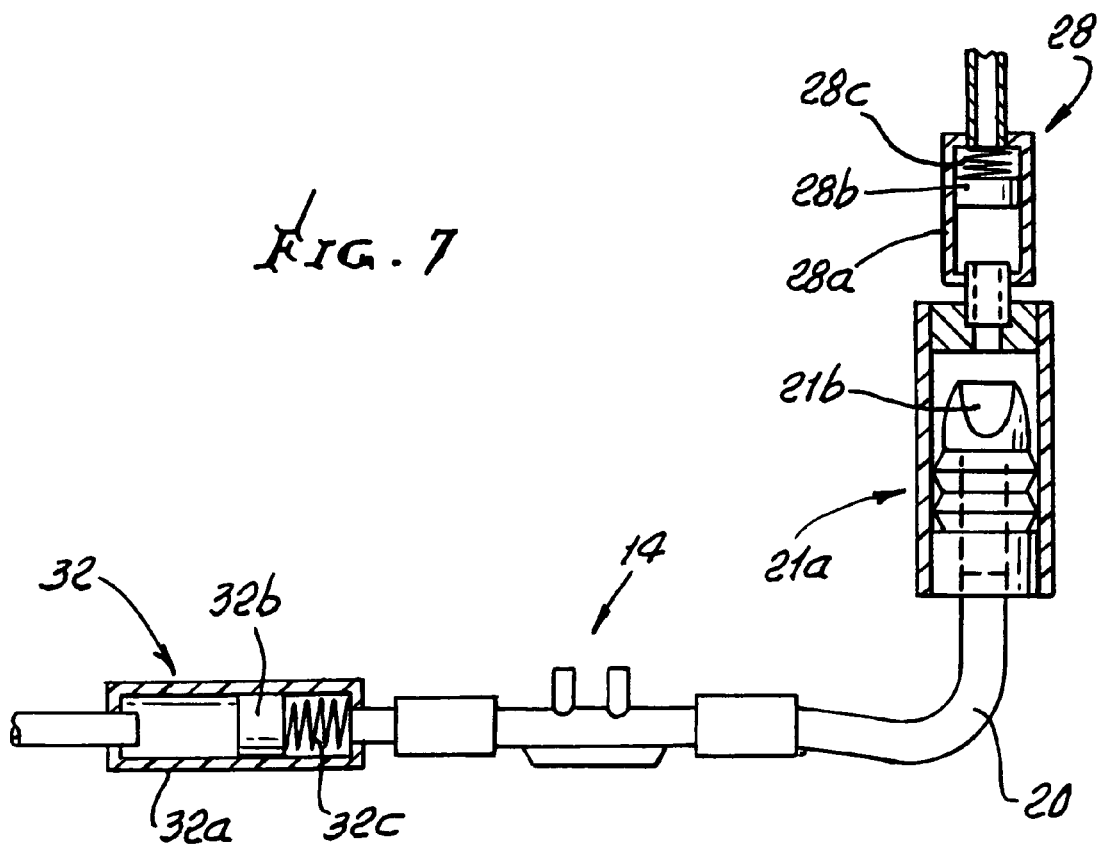
FIG. 7 is a view like FIG. 6, but also showing an additional flow meter downstream of the pressure relief valve.

The invention also contemplates provision and operating of flow metering third means, indicated at 28 in FIGS. 1 and 5, downstream of the cannula 14, and downstream of the second means 21$a$; and/or provision and operation of flow metering first means, indicated at 32 in FIG. 6, in the ducting upstream of the nasal cannula 14. FIG. 7 shows use of both 28 and 32 in the system ducting. These elements typically have visible flow rate readouts, at the sides of transparent tubing 28*a* and 32*a*, containing pistons 28*b* and 32*b* which shift position lengthwise in the tubing, as flow rates vary, to indicate such rates. Air flow pressure pushes such pistons against compression springs 28*c* and 32*c*. If indicated flow at 28 shows loss of flow at 14, the flow at 11 can be adjusted to compensate for the loss to atmosphere at 21*a*, consistent with the infant's or patient's lungs. Such indicated rates, prior to adjustment, could for example be too low as a result of excessive leaking at the infant's nostrils or mouth.

Figure 3:
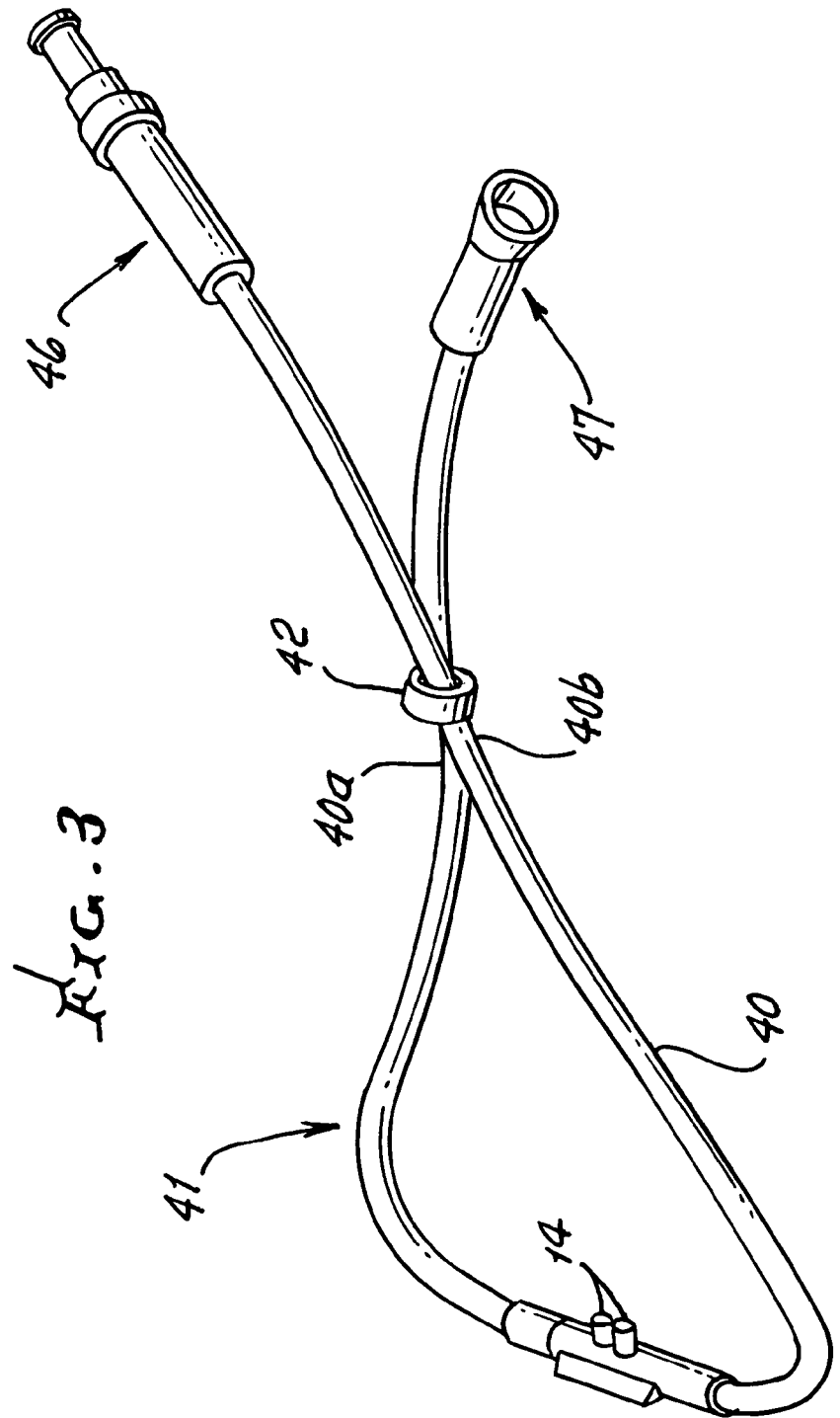
FIG. 3 is a perspective view showing actual elements of the system.

FIG. 3 shows the ducting to include plastic tubing 40 forming a loop 41, as a result of a clasp 42 loosely grasping tubing portions 40*a* and 40*b* permitting relative slippage to contract or enlarge the loop, around the infant's head, for holding cannula prongs 14 in the nostrils. Note inclusion of the proportioning valve enclosure 46, in series with the tubing. Fixture 47 connects the tubing to system ducting downstream of the heater humidifier 15.

Figure 2:
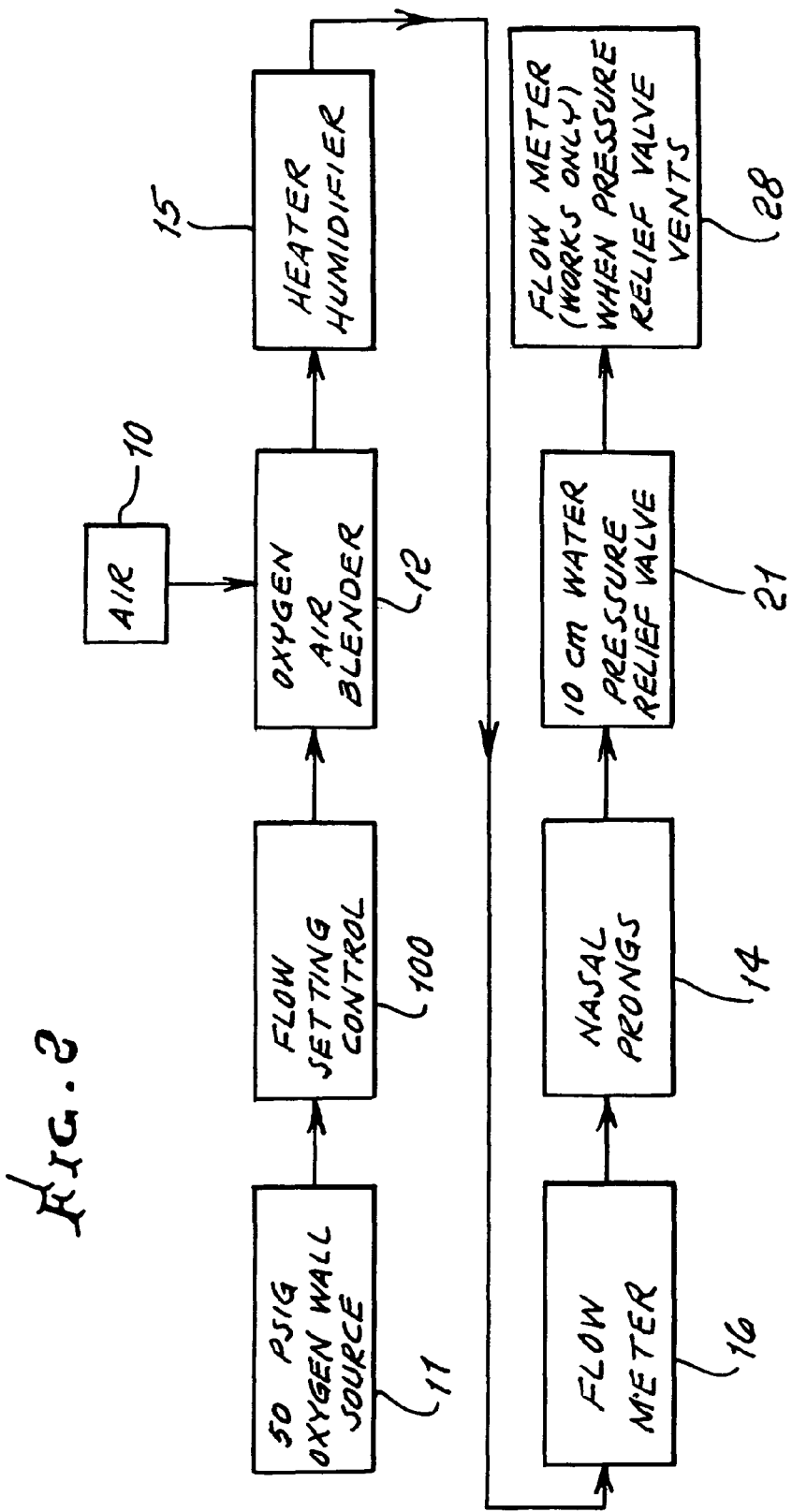
FIG. 2 is a system block diagram.

FIG. 2 is a block diagram of the system.

We claim:

1. A combination control for use in nasal cannula therapy, comprising
   a) a nasal cannula respiratory assistance ducted apparatus,
   b) said apparatus including the following ii) proportioning second valve means and at least one of the following i) flow metering first means and iii) flow metering third means:
   i) said flow metering first means upstream of the nasal cannula,
   ii) said proportioning second valve means also associated with said apparatus ducting, serving as a safety release valve, downstream of the nasal cannula,
   iii) said flow metering third means associated with the apparatus ducting, and downstream of the nasal cannula.

2. The combination of claim 1 includes, in series sequence
   i)' an oxygen gas source,
   ii)' means receiving oxygen from said source, and air, for blending air and oxygen and/or nitric oxide in an output stream,
   iii)' a heater/humidifier to heat and humidify said stream,
   iv)' said nasal cannula to receive the heated and humidified stream,
   v)' said i), ii) and iii) means, as defined.

3. The combination of claim 1 wherein said nasal cannula comprises a by-pass outlet from the apparatus ducting for air and oxygen flow to the patient's nose, downstream of said first means.

4. The combination of claim 2 wherein said nasal cannula comprises a by-pass outlet from the apparatus ducting for air and oxygen flow to the patient's nose, downstream of said first means.

5. The combination of claim 3 wherein said ii) means comprises a proportioning valve positioned for discharging excessive-pressure air and oxygen blend from said ducting.

6. The combination of claim 4 wherein said ii) means is positioned for discharging excessive-pressure air and oxygen blend from said ducting.

7. The combination of claim 3 wherein said ducting includes plastic tubing forming a loop, said bypass outlets projects from the loop, and a holder clasping two portions of the tubing to form the loop.

8. The combination of claim 1 wherein said included flow metering first means or flow metering third means comprises a flow metering element in ducting hem apparatus.

9. The combination of claim 1 wherein said included flow metering first means and flow metering third means comprises flow metering elements in spaced apart sections of the ducting.

10. The combination of claim 1 wherein said flow metering first means is located upstream of said proportioning second valve means.

* * * * *